US00PP22986P3

(12) United States Plant Patent
Bautista

(10) Patent No.: US PP22,986 P3
(45) Date of Patent: Aug. 21, 2012

(54) ***HELICHRYSUM* PLANT NAMED 'HARVEST MERLOT'**

(50) Latin Name: ***Helichrysum bracteatum*×*splendidum***
Varietal Denomination: Harvest Merlot

(75) Inventor: Rodolfo Valdoz Bautista, Half Moon Bay, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 12/925,210

(22) Filed: Oct. 15, 2010

(65) Prior Publication Data

US 2012/0096613 P1 Apr. 19, 2012

(51) Int. Cl.
*A01H 5/00* (2006.01)

(52) U.S. Cl. ..... Plt./359
(58) Field of Classification Search ..... Plt./359
See application file for complete search history.

*Primary Examiner* — June Hwu
*Assistant Examiner* — Louanne Krawczewicz Myers
(74) *Attorney, Agent, or Firm* — James R. Cypher; Charles R. Cypher

(57) ABSTRACT

A plant variety of the *Helichrysum* family resulting from a controlled crossing of the varieties of *Helichrysum bracteatum* 'Harvest Fire', the subject of a currently pending U.S. patent application, and *Helichrysum bracteatum*×*splendidum* 'Raspberry', the subject of U.S. Plant Pat. No. 19,929. The outermost involucral bracts of the bud appear as RHS 64 B (red-purple group). The rest of the bracts have an overall appearance of RHS 58 A (red-purple group). The tips of the outer bracts are RHS 187 A (greyed-purple group). The new variety also possesses the commercially desirable characteristics of hardy and attractive leaves and has generally good post harvest characteristics.

2 Drawing Sheets

Botanical classification: *Helichrysum bracteatum*×*splendidum.*

Variety denomination: 'Harvest Merlot'.

BACKGROUND OF THE INVENTION

The present invention relates to a new and distinct variety of the Compositae family. The new variety is named *Helichrysum bracteatum*×*splendidum* 'Harvest Merlot'.

This new *Helichrysum* variety originated as a seedling from the progeny of a controlled hybridization conducted by the inventor in a commercial nursery in the city of Half Moon Bay. Half Moon Bay is located in San Mateo County, on the northern coast of California.

The inventor crossed *Helichrysum bracteatum* 'Harvest Fire', the subject of a currently pending U.S. patent application, with *Helichrysum bracteatum*×*splendidum* 'Raspberry', the subject of U.S. Plant Pat. No. 19,929, to produce the new variety. 'Raspberry' was the pollen parent, and 'Harvest Fire' was the seed parent. The pollen parent 'Raspberry' is itself the result of a controlled hybridization. 'Raspberry' was produced by crossing *Helichrysum bracteatum bracteatum*× *splendidum* 'Harvest Plum', the subject of U.S. Plant Pat. No. 10,742, with *Helichrysum bracteatum bracteatum*×*splendidum* 'Lemon', the subject of U.S. Plant Pat. No. 19,976. In the cross that produced 'Raspberry', 'Harvest Plum' was the seed parent. 'Harvest Fire', the seed parent of the new variety, is itself the result of a controlled hybridization. 'Harvest Fire' was produced when *Helichrysum bracteatum bracteatum*× *splendidum* 'Raspberry', the subject of U.S. Plant Pat. No. 19,929, was crossed with *Helichrysum bracteatum* (Venten.) Andr. 'Harvest Nectarine', the subject of U.S. Plant Pat. No. 10,834. In the cross that produced 'Harvest Fire', 'Raspberry' was the seed parent. The new variety was selected for commercial development because of its unique flower head color, the hardiness and attractiveness of its leaves and its generally good post harvest characteristics.

The new variety is suitable for commercial plant culture because of its long-lasting flowers, attractive coloring and compact growth habit. The desirable and unique combination of characteristics of the new variety include:

the color of its flower head and bud,
its dense and attractive foliage that resists yellowing,
its compact growth habit, and
its ability to grow and thrive as a commercial plant for sale.

The infloresence is made up of a number of involucral bracts, surrounding a disk head. The base of the outer bracts are not pigmented. The pigmentation is the same for both the abaxial and the adaxial sides of the bracts. The outermost involucral bracts of the bud appear as RHS 64 B (red-purple group). The rest of the bracts have an overall appearance of RHS 58 A (red-purple group). The tips of the outer bracts are RHS 187 A (greyed-purple group).

The following table compares the new variety to the closest varieties known to the inventor and its parents.

TABLE 1

| | *H. bracteatum* (general characteristics) | 'Raspberry' U.S. Plant Pat. No. 19,929 | 'Harvest Nectarine' U.S. Plant Pat. No.10,834 | 'Harvest Fire' patent pending |
|---|---|---|---|---|
| Bract color | Various colors | R.H.S 58 D (red-purple group) | Bract tips: R.H.S. 34A (orange-red group). Bract base: | Involucral bracts at opening are predominantly R.H.S. 22A |

TABLE 1-continued

| | | | | |
|---|---|---|---|---|
| | | | R.H.S. 21C (yellow-orange group). Base color dominates in innermost bracts. | (yellow-orange group). Upper involucral bracts when flower head is mature are predominantly R.H.S. 9A (yellow group). |
| Bud color | Various colors | R.H.S. 187 D (greyed-purple group) | | R.H.S. 26A |
| Leaf Surfaces | Puberulent | Puberulent | Puberulent | Puberulent and sparsely villous, main veins are hirsute |
| Suitability for pot culture | Good | Good | Good | Good |
| Ease of forcing | Generally good | Good | Good | Good |
| Growth habit | Generally compact | Compact | Good | Compact |

| | 'Harvest Plum' U.S. Plant Pat. No. 10,742 | 'Lemon' U.S. Plant Pat. No. 19,976 | New Variety 'Harvest Merlot' |
|---|---|---|---|
| Bract color | Bract tips: R.H.S. 66D (red -purple group). Bract base: R.H.S. 155C (white group). Tip color dominates in all but innermost bracts. | R.H.S 5 B (yellow group). | The outermost involucral bracts of the bud appear as R.H.S. 64 B (red-purple group). The rest of the bracts have an overall appearanceof R.H.S. 58 A (red-purple group). The tips of the outer bracts are R.H.S. 187 A (greyed-purple group). |
| Bud color | Bract tips: R.H.S. 187A (greyed-purple group. Bract base: R.H.S. 67B (red-purple group) | R.H.S. 160 D (greyed-yellow group) | R.H.S. 187 A (greyed-purple group) |
| Leaf Surfaces | Puberulent | Puberulent | Puberulent |
| Suitability for pot culture | Good | Good | Good |
| Ease of forcing | Good | Good | Good |
| Growth habit | Compact | Compact | Compact |

The distinguishing characteristics are retained by asexually reproduced, successive generations. The inventor, at a commercial nursery in Half Moon Bay, Calif., has asexually reproduced the new variety through three successive generations by means of cuttings and has found that the combination of characteristics as herein disclosed remain firmly fixed.

BRIEF DESCRIPTION OF THE DRAWINGS

The accompanying drawings consist of color photographs that show the typical potted-plant form, including the inflorescence, foliage, and bract color development from the bud stage to the mature flower head. The colors are represented as truly as possible using conventional photographic procedures.

DETAILED DESCRIPTION OF THE NEW VARIETY

Figure 1:
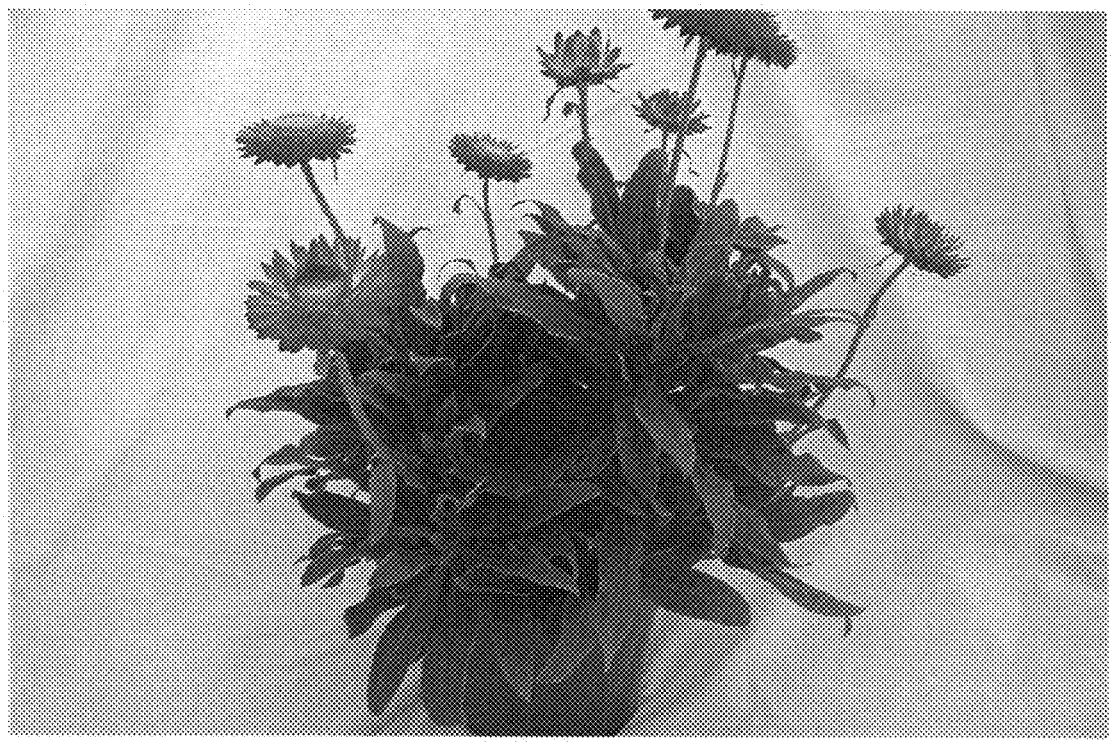
FIG. 1 is a perspective view of a potted plant of the new variety described herein, illustrating the overall form and appearance of the plant in full bloom.
Figure 2:
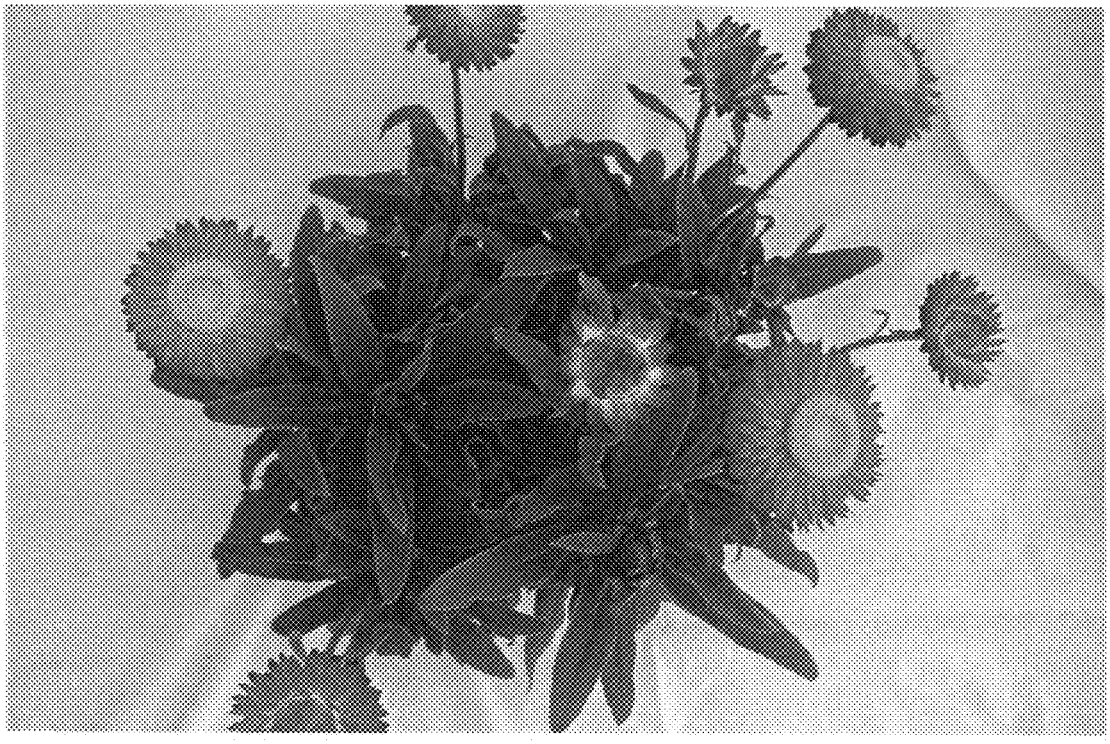
FIG. 2 is a top view of a potted plant of the new variety described herein, illustrating the overall form and appearance of the plant in full bloom.
Figure 3:
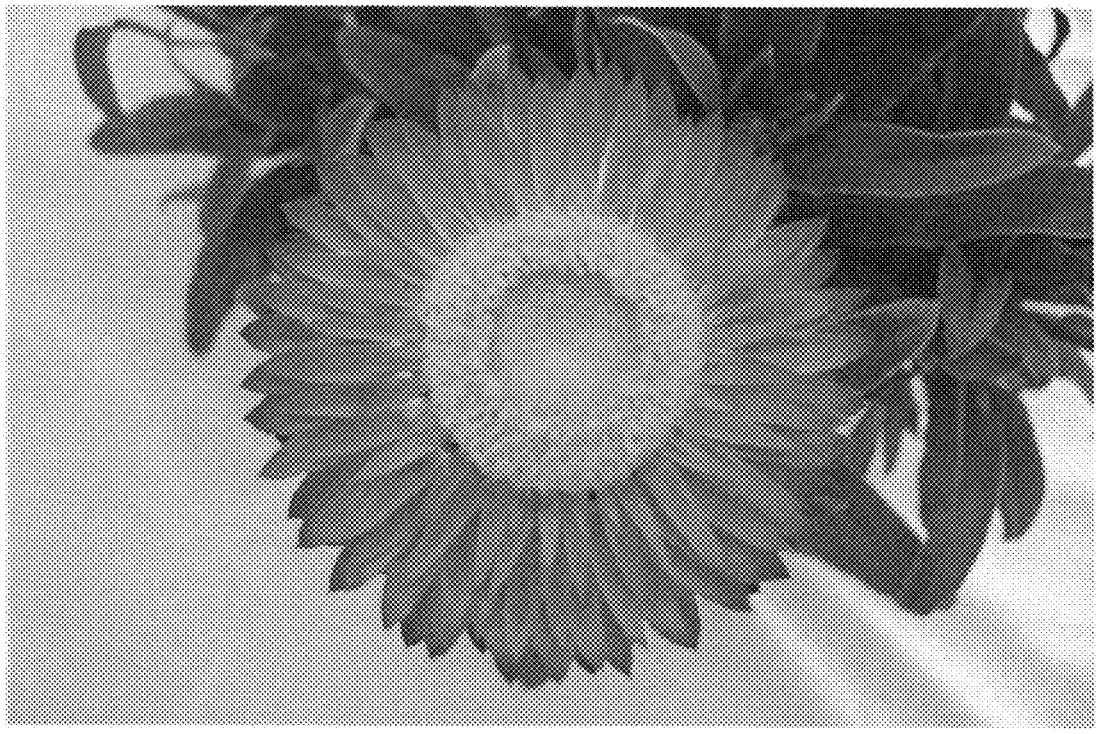
FIG. 3 is a top view of a mature flower head of the new variety.
Figure 4:
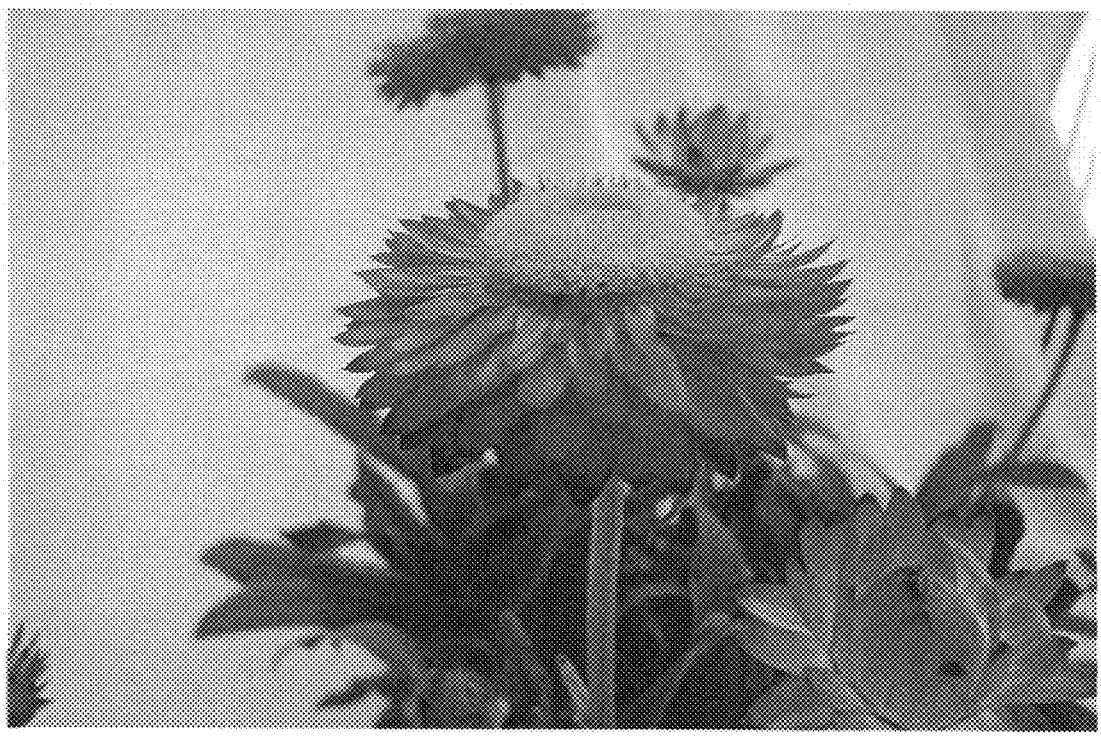
FIG. 4 is a side view of a mature flower head of the new variety.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to the R.H.S. Colour Chart published by The Royal Horticultural Society of London, England, in association with the Flower Council of Holland, located in Lieden.

The following description is based on observations of optimally fertilized plants grown in 6" pots.

Cuttings were taken from mature plants and placed in cells. Plants were transplanted to 6" pots approximately 6 to 8 weeks after root initiation occurred. The plants were then started in the green house for 2 to 3 weeks, pruned, and then moved outside for 10 to 12 weeks to bloom.

The observed plants were approximately 20 weeks old.

The plants were grown under glass in Half Moon Bay, Calif. The day time temperature in the green house where the plants were grown was kept between 65 and 73 degrees Fahrenheit during the day and 65 degrees Fahrenheit at night. The humidity was maintained at 90%.

THE PLANT

Name: *Helichrysum bracteatum×splendidum* 'Havest Merlot'.

Origin: Seedling.

Parentage: *Helichrysum bracteatum* 'Harvest Fire', the subject of a currently pending U.S. patent application, with *Helichrysum bracteatum×splendidum* 'Raspberry', the subject of U.S. Plant Pat. No. 19,929. 'Raspberry' was the pollen parent, and 'Harvest Fire' was the seed parent.

Classification:

*Family*.—Compositae.

*Tribe*.—Inula.

*Genus*.—*Helichrysum*.

*Species*.—*Helichrysum bracteatum×splendidum*.

*Commercial*.—Strawflower.

Form: Upright, compact, biennial herb.

Height: Plant grown in 6" pot is 35 cm.

Diameter: Plant grown in 6" pot is 35 cm.

Growth: Upright, vigorous growth under glass with excellent branching; easily forced to bloom without growth regulators.

Stems:

*Texture*.—Generally, stems are moderately pubescent at their base; stems are very sericeous below the flower, making for a glaucous appearance.

*Shape*.—Stems have a rectangular cross section below the base of the flower becoming round at base.

*Size*.—Stem width at top of plant below the terminal flower head is 5 mm. The stem widens in one direction to accommodate axilary stems, becoming approximately 10 mm wide. Where stems meet the original cutting, the stems are approximately 8 mm to 11 mm wide. Main stem is 35 cm in height, lateral branches range from 20 to 30 cm in height. Leaves are basal at new growth on the main stem and at base of lateral branches.

*Color*.—The diameter of the original cutting is 15 mm. Stems at base of plant are woody — RHS 199 C (gray-brown group). The first portions of the stem that are not woody are RHS 139 D (green group).

Foliage:

*Quantity*.—Abundant.

*Shape*.—Linear; narrowly acute at the leaf's apex and base; margins are entire by wavy so they appear repand; pinnately veined, and basaly attached to the stem with no distinct petiole.

*Size*.—As large as 16 cm long by 30 mm wide.

*Texture*.—Viscid; main vein dominates on the underside of leaf and is sunken on the leaf surface.

*Pubescence*.—Both the upper and lower surfaces of the leaves are puberulent.

*Color*.—Upper leaf surface is RHS 137A to 137 B (green group); lower leaf surface is RHS 137C (green group).

Disease resistance: Roots appear to be disease resistant.

The Bud

Form: Conical, with imbricate involucral bracts. It is the color of the outermost involucral bracts as RHS 187 A (greyed-purple group) that provide the color of the buds.

*Size*.—When fully.

Texture: Smooth and glossy (waxy).

Rate of opening: Slowly, and in layers, closing at night; fully open in 2-3 weeks.

Involucral bracts:

*Color*.—Outermost involucral bracts are RHS 187 A (greyed-purple group).

*Aspect*.—Thin, dry, membranous.

The Inflorescence

Form: Flower head is discoid and solitary; usually 1 or 2 buds at the next leaf axis below which is usually 12 to 15 cm below. Inflorescences are persistent, opening very slowly. The inflorescences become desiccated as they mature, but do not wither or fall from the plant, and remain attractive even in their desiccated state, making them an attractive potted plant. The inflorescences typically last 8-12 weeks. Initially 8 to 12 inflorescences will appear on a plant with more arising as lateral buds develop. Plants are typically grown for flowering in August, as was the case with the observed plants. In California, the new variety flowers year round with more blooms appearing in the summer months. Young plants can be forced to flower in any season in California.

Flower head size:

*Diameter*.—55 mm. Disc floret portion diameter: 24-25 mm.

Shape of the flower head: Circular; involucral bracts are numerous and imbricate.

Appearance of the flower head: Showy.

Involucral bracts:

*Form*.—Involucral bracts are imbricate in many rows. Involucral bracts are scarious and membranous, but are brightly colored. The involucral bracts are deltoid, enlarged and petal-like. The apex is acute, the margins entire and the base truncate. The pigmentation is the same for both the abaxial and the adaxial sides of the bracts. The outermost involucral bracts of the buds are RHS 187 A with the color of the tip dominating when the buds are still small and only the outermost bracts are visible. As the inflorescence matures and enlarges, the tips of the outermost involucral bracts remain RHS 187 A; however, the main color of the outermost bracts develops to RHS 64 B (red-purple group) and their base is white which is typical for this plant and its immediate ancestors. The rest of the bracts have an overall appearance of RHS 58 A (red-purple group).

*Size and number*.—Involucral bracts range from 10 mm to 20 mm long and 3 mm to 10 mm wide, and there can be as many as 100 involucral bracts on a flower head.

Disc florets:

*Form*.—Florets are all small, bisexual and tubular. The corolla of the florets is usually 5-lobed. Corolla is usually 7-9 mm long and glaucous (waxy). The corolla tube is approximately 1 to 2 mm in diameter just below its apex. The upper 3.5 mm of the corolla is usually brightly colored, RHS 24 A (orange group), the remainder of the corolla along with the gynoecium is RHS 155 D (white group). The protruding portions of the pistil, the stamens and pollen are similarly colored.

*Androecium*.—There are usually 5 stamens borne on the corolla tube. The stamens, including the anthers, are usually united into a tube around the style and become highly reflexed from the point of separation. The stamens protrude from the corolla and are typically 7 to 9 mm. Pollen occurs on the adaxial surface of the anthers.

*Gynoecium*.—One pistil per disc floret. The ovary is inferior, and approximately 2 mm tall. The style is often branched. The style protrudes from the corolla about 2 to 3 mm. There is a pappus with many bristles. The bristles are approximately 8 mm long. Color of the bristles is RHS 10 D (yellow group).

Fragrance: None.

Achenes: The achenes rarely germinate.

I claim:

1. A new and distinct variety of *Helichrysum* plant, as illustrated and described.

* * * * *